United States Patent
Ritsche et al.

(10) Patent No.: US 6,484,715 B1
(45) Date of Patent: Nov. 26, 2002

(54) MEDIA DISPENSER (75) Inventors: Stefan Ritsche, Radolfzell; Stefan Käfer, Eigeltingen, both of (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 0 days.

(21) Appl. No.: 09/351,711

(22) Filed: Jul. 12, 1999

(30) Foreign Application Priority Data

Jul. 14, 1998 (DE) .......................................... 198 31 525

(51) Int. Cl.[7] .............................................. A61M 11/00
(52) U.S. Cl. ............................. 128/200.21; 128/200.23
(58) Field of Search ........................ 128/200.21, 200.23, 128/203.12, 203.14, 203.15, 203.21–203.24

(56) References Cited

U.S. PATENT DOCUMENTS

| | | | | |
|---|---|---|---|---|
| 4,524,769 A | * | 6/1985 | Wetterlin | 128/203.15 |
| 4,627,432 A | * | 12/1986 | Newell et al. | 128/203.15 |
| 4,811,731 A | * | 3/1989 | Newell et al. | 128/203.15 |
| 5,201,308 A | * | 4/1993 | Newhouse | 128/203.15 |
| 5,331,953 A | * | 7/1994 | Andersson et al. | 128/200.14 |
| 5,349,947 A | * | 9/1994 | Newhouse et al. | 128/203.21 |
| 5,372,128 A | * | 12/1994 | Haber et al. | 128/203.21 |
| 5,505,193 A | * | 4/1996 | Ballini et al. | 128/200.15 |
| 5,529,059 A | * | 6/1996 | Armstrong et al. | 128/203.12 |
| 5,533,502 A | * | 7/1996 | Piper | 128/203.21 |
| 5,542,411 A | * | 8/1996 | Rex | 128/203.15 |
| 5,622,166 A | * | 4/1997 | Eisele et al. | 128/203.12 |
| 5,657,748 A | * | 8/1997 | Braithwaite | 128/203.15 |
| 5,673,685 A | * | 10/1997 | Heide et al. | 128/203.15 |
| 5,685,294 A | * | 11/1997 | Gupte et al. | 128/203.15 |
| 5,740,794 A | * | 4/1998 | Smith et al. | 128/203.15 |
| 5,785,049 A | * | 7/1998 | Smith et al. | 128/203.15 |
| 5,794,613 A | * | 8/1998 | Piskorski | 128/203.12 |
| 5,881,719 A | * | 3/1999 | Gottenauer et al. | 128/203.15 |
| 5,924,417 A | * | 7/1999 | Braithwaite | 128/203.15 |
| 5,964,417 A | * | 10/1999 | Amann et al. | 128/203.21 |
| 5,975,076 A | * | 11/1999 | Yianneskis et al. | 128/203.15 |
| 5,983,893 A | * | 11/1999 | Wetterlin | 128/203.15 |
| 6,065,471 A | * | 5/2000 | Schaeffer et al. | 128/203.15 |
| 6,065,472 A | * | 5/2000 | Anderson et al. | 128/203.21 |
| 6,116,238 A | * | 9/2000 | Jackson et al. | 128/203.15 |
| 6,116,239 A | * | 9/2000 | Volgyesi | 128/203.15 |

FOREIGN PATENT DOCUMENTS

DE 197 04 849 A1 2/1997
WO WO 96/33759 10/1996

* cited by examiner

Primary Examiner—John G. Weiss
Assistant Examiner—Teena Mitchell
(74) Attorney, Agent, or Firm—Quarles & Brady LLP (57) ABSTRACT

A dispenser (1) has two remote pressure handles (29, 35) and lateral gripping recesses (58) for mutually displacing two units (2, 3) axially and rotationally. A tear-off web (52) prevents the two units (2, 3) from being actuated accidentally. A discharge stud (34) protrudes beyond the handles (29, 35, 58). The dispenser (1) is so small that it may be fully enveloped and covered by one user's hand. Nevertheless reliable actuation for nasal application is assured.

19 Claims, 3 Drawing Sheets

MEDIA DISPENSER

TECHNICAL FIELD AND BACKGROUND OF THE INVENTION

The invention relates to a dispenser for discharging flowable or other media which may be gaseous, pasty or liquid, preferably powdery. On dispensing the dispenser is held and simultaneously operated single-handedly. The medium is hauled by suction or inhalation. Thereby the pharmaceutical active substance contained therein may be inhaled or deposited on the mucous membrane of the patient's nose. The dispenser may be made entirely of injection-molded or plastics parts.

OBJECTS OF THE INVENTION

An object is to provide a dispenser which obviates the draw-backs of known configurations. Another object is to permit microvolumetrical delivery. A further object is to provide a miniature dispenser, which i.e. can be single-handedly clasped and therewith entirely enveloped or covered. Still another object is to provide a dispenser which is simple to manufacture, assemble, handle, keep, or the like.

SUMMARY OF THE INVENTION

According to the invention the dispenser is suitable for accommodating a blister pack comprising exclusively two store chambers. The deep-drawn store cups and a deck plate thereof are made of a transparent plastics film or of a metal foil such as aluminum. The cup walls are substantially thinner than the foil deck, the thickness of which is less than half a millimeter. The cup openings are hermetically sealed by a film of plastics or metal foil, such as aluminum, which is thinner as compared to the cup and deck. The planar sealing film or foil is thermoplastic-welded to the planar deck. The sealing foil forms in a knurled pattern protuberances which in forming corresponding indents are undetachably melted to the deck. Beyond the deck's rear side only the cups protrude, thus lending themselves to good support. The clearance between the cups is at least 1.5 times larger than the cup diameter which is greater than the cup depth. The axes spacing between the cups is less than 30 mm or 25 mm.

The dispenser has lateral external depressions or a waisting enabling each base body to be reliably gripped between thumb and index finger, e.g. when setting or twisting one base body relative to the other. Such depressions also form the remote pressure faces for axially shortening the dispenser.

The store cup is directly supported with respect to the base body with zones adjoining its margin rim with its outer circumference or with its bottom. Thus its positioning is precise. Thereby too the cup is protected against damage by support and shielding.

To precisely rotationally orient the two base bodies and the store body or blister pack relative to each other a snap connection or a resilient catch is provided. This latch acts likewise in the various mutual axial positions of these three bodies. The catch members may also overcomeably lock in one or more mutual axial positions of the three bodies. Each latched position is prevailable by a correspondingly high twist or axial input force. Apart from the locked positions the bodies are difficult to be mutually twisted due to increased friction. In the locked position yet a slight and more easily mobile rotative play is provided.

The initial or rest position for actuation lies between the rotation permitting position and the actuated end position. A latch needs to be overcome to transfer from the rest position to the rotation permitting position. This latch may be formed by mutually overlapping rims of the base bodies. In the rotation permitting position a captive stop prevents withdrawal. By exerting an increased force this stop too, namely a snap connection, is overcomeable to permit mutual separation of the base bodies. When moving from the rest position to the end position no latching resistance has to be overcome, but merely the rupture resistance of the foil seal and the frictional resistance between the base bodies. In this end position a freely protruding discharge stud is at least as long as the remainder of the dispenser.

The dispenser is tamper-proof to the extent that although a blister pack is to be inserted without altering or ruining the tamper-proof safeguard, the blister pack cannot be then opened. The safeguard fully surrounds a rim of that base body which externally overlaps. The safeguard is in dust-tight contact with this rim which does not overlap the other body in the latched position. Thus these bodies can be instantly mutually twisted without mutual axial motion once the safeguard has been detached. When the base bodies are then mutually perpendicularly oriented the blister pack or its reception is then freely visible. This is also the case when one of the two base bodies is made of a transparent or translucent material.

The blister pack is safeguarded from being extracted axially by positively acting means which can only be overcome by exerting an increased manual force. This safeguarding for firstly the blister pack and for secondly mutually the base bodies act independently of each other and of the tamperproof safeguard.

Including each of the cited safeguarding means and without the blister pack the dispenser comprises only two one-part components. No return spring is needed for mutually moving the components. Reference is made to the German patent application 197 04 849.8 (=PCT/EP 9800311) in including the features and effects thereof in the present invention.

The described or another dispenser is suitable for receiving and storing biological active substances over several weeks, months or years. These may be physiologically active substances such as hormonal active substances and/or active substances containing breakdown or fission products such as peptides from proteins. Such biological information transmitters when containing amino acids or other similar active substances may be highly sensitive to moisture. Therefore the substances are thus held in the dispenser in a pressure-proof or sealed chamber. This chamber is not opened until immediately before being discharged from the dispenser, e.g. by destroying a seal.

BRIEF DESCRIPTION OF THE DRAWINGS

Example embodiments of the invention are explained in more detail in the following and illustrated in the drawings in which.

DETAILED DESCRIPTION

The dispenser 1 has two units 2, 3 to be translated without mutual rotation from a rest position (FIG. 1) to an end position with the dispenser 1 shortened. Without simultaneous change in length units 2, 3 are mutually rotatable in the rest position over more than 360°. First unit 2 consists of only a beaker-type base body 2 and a blister pack or store body 6 located totally therein. Second unit 3 consists of only a base body 5. Each base body 4 or 5 is in one part.

Dispenser 1 serves to accommodate only two separate dosages of the medium to be discharged one after the other and held in separate blisters or stores 7. The volume of cup 7 is more than four, six or eight times greater than the medium contained therein. On discharge, the medium flows through store 7 directly in a straight outlet duct 8, the circular disk-shaped cross-sections of which continually increase at an acute angle in the flow direction. Its outer end forms the medium outlet 9 and has a diameter of at least 3 mm or 5 mm, as compared to which the largest cup width is greater but smaller than 2.5 and 1.5 times the said diameter. On discharge, duct 8, outlet 9 and the one store 7 have a common axis 10 oriented parallel to the setting axis 11, to the discharge direction 12 and to the actuating direction 13. The center or symmetry axis of units 1 to 6 is located in two planes of symmetry oriented at right angles to each other, to which the setting or rotation direction 14 is oriented at right angles.

Each store 7 comprises a dished store cup 15, the planar opening of which is sealed off pressure-hermetically by a store closure 16, namely a planar blister diaphragm. The spherically domed cup bottom 17 translates smoothly into a store jacket 18 which is conically acutely flared toward the store opening. Shell 18 translates directly into the planar deck plate 19 which is totally covered by the closure 16 adhesively connected thereto.

Between the integral stores 7 the deck 19 is traversed by a support body 20 which is telescopic and comprises only two parts. Cups 15 are radially spaced from the hollow or tubular support body 20, the outer circumference of which is formed by a freely protruding projection 21 of body 4. Rim 22 of deck 19 is supported on all sides by an inner support shoulder 23 of body 4. Between stores 7 the deck 19 is supported along a central opening by a ring shoulder of the mandrel or spigot provided by projection 21. Thus the micro-thin cups 15 are positionally locked with zero clearance when its corresponding chamber 24 is emptied. When body 6 is separated, the walls of the store cups 15 and the deck 19 are bendingly flexible or elastic.

In plan view body 4 forms an oblong cap 25 including an outermost jacket 26 and a bottom 27. Each cup 15 is spaced from both walls provided by jacket 26 and bottom 27. Relative to the open, planar end face of the shell formed by jacket 26 the support face or shoulder 23 is countersunk by at least twice or maximally five or four times the thickness of deck 19. In the common axial plane 60 of axes 10, 11 projection 21, jacket 26 and bottom 27 are stiffened by ribs 28 adjoining them directly. The free rib edges are coplanar with support shoulder 23 and likewise support deck 19. Each member 28 has a recessed reception 62 which is spaced from and located between the shell provided by projection 21 and the jacket 26. Bottom support or reception 62 is snugly adapted to the outer shape of cup 15 and thus provides direct strip-shaped support for the zones provided by cup bottom 17 and store jacket 18.

On inserting store body 6 it is the central opening in deck 19 that first engages the centering end of projection 21. Thereafter deck 19 and both cups simultaneously engage support shoulder 23 and reception 62. Thereby a safeguard 63 is activated in positively preventing body 6 from lifting off by its weight from support shoulder 23 and reception 62 when unit 2 is turned upside down. Safeguard 63 has snap projections on the inner circumference of the rim of jacket 26. These projections 63 protrude beyond support shoulder 23 and can radially resiliently shunt when rim 22 is held without motion play between projections 63 and support shoulder 23. Thereby body 6 does not protrude beyond the opening of jacket 26.

Body 6 is prevented from rotation relative to body 4 not only by contacting the inner circumference of jacket 26 but also by engaging projection 21. Therefore the opening in deck 19 deviates in shape from circular. This shape includes a circle with two opposing flats or with counterdirectional cut-outs. The insertion end of projection 21 is complementarily adapted to this shape. The outside of wall 27 and projection 21 commonly form a recessed actuating handle 29. Projection 21 adjoins in one part only to the inside of wall 27. Actuating handle 29 is concave and extends up to the outsides of both length sections of jacket 26. Thus handle 29 can be centeringly supported on the side of the last joint of the user's index finger beyond which both store places then freely protrude.

Support body 20 provides a connection or plug reception simultaneously forming the central telescopic connection between bodies 4, 5. Support body 20 is totally concealed from outside in every relative position of bodies 4, 5. Support body 20 serves as a permanent rotational bearing 30, as a plug connection between bodies 4, 5 and for their mutual axial guidance on actuation. Body 5 forms a cap 31 likewise oblong parallel to plane 60. Shell 32 of cap 31 protrudes from end wall 33 counter jacket 26 toward wall 27. The inner circumference of shell 33 is closely adapted to the outer circumference of jacket 26. The free end face of projection 21 abuts on the inside of end wall 33 at the stroke end. Then slots or respective suction ducts 55 are free between the insides of walls 32, 33 and the outsides of the walls provided by jacket 26 and support deck 19. Suction ducts 55 guide ambient air flowing radially toward axis 10 in a jacket flow about chamber 24. Then the air is led into chamber 24 in direction 13. From here the air entrains the medium back in direction 12 and directly out of opening 9. Suction may also occur through support body 20 or bearing 30 and thereby be variably throttled by the cited user's finger, since the passage of projection 21 traverses wall 27 only in the vicinity of handle 29.

Shell 32 and end wall 33 transit into a discharge stud 34. Stud 34 freely protrudes in direction 12 beyond the planar portion of wall 33 by more than the length of shell 32, e.g. by at least 1.5 or 2 times thereof. On both sides of plane 60 and on its side remote from wall 33 the outer shell 38 of stud 34 transits directly into shell 32 by an arc angle of at least 1800 or more without any intermediate shoulder. With the outside shell 38 transits into wall 33 concavely curved. There shell 38 forms a deepened actuating handle 35 axially congruent with handle 29. Handle 35 has projections enhancing the grip and serves to support the user's thumb tip which can simultaneously support on wall 33 and on the outer circumference of stud 34. A bearing mandrel 36 protrudes from the inside of wall 33 and is closely adapted to the inner circumference of projection 21. Arbor 36 extends up to handle 29 in the actuated end position.

Handle 29 supports on the user's middle finger and the handle 35 supports on the thumb of the same hand. Thus this hand's index finger can support on the outer circumference of stud 34. Thereby the dispenser 1 can be reliably oriented. Arbor 36 protrudes beyond the end of shell 32 and is surrounded by the stop for projection 21. Thus, on closing the housing provided by caps 25, 31 firstly its mandrels respective projection 21 and arbor 36 interengage. Body 6 may also be first plugged on arbor 36. On closing the casing body 6 is automatically slipped over projection 21 due to inclined faces involved on closure of the housing. Projection 21 and arbor 36 freely protrude counterdirectionally.

Stud 34 also has an inner shell 37 freely protruding counter direction 13 up to the open end face of cap 31. Shell 37 has a wall thickness steadily reduced in direction 13 up to its inner end. The outer end of shell 37 adjoins in a ring zone and in one part the outer end of shell 38. This ring zone bounds outlet 9. Tube 37 bounds duct 8 and is free of contact with shell 38 except for the ring zone. At its outer circumference tube 37 has four axial ribs 39 circumferentially uniformly distributed. Ribs 39 are located in axial planes inclined at an angle of 45° to plane 60. Ribs 39 do not adjoin the inner circumference of shells 32, 38. The length of stud 34 above end wall 33 is at least as great as the spacing between handles 29, 35 when in the shortened end position. The annular end face of stud 34 is rounded at its outer circumference with a radius greater than that at its inner circumference.

Both store chambers 24 are commonly closed by foil 16 totally covering deck 19. For opening, the free end of tube 37 forms a rectangularly conical tool 40. The tool spike 41 transits into diverging webs 42 which adjoin the end face of tube 37 in the middle between ribs 39. Between adjacent parting members 42 in each case a port 44 of a duct inlet 43 is located. In the shortened end position cup 15 is totally out of contact with parts 37, 40. Air drawn in via the paths or suction ducts 55 enters via the annular duct between shells 18, 37 into chamber 24 where it forms a roller swirl to flow from the swirl directly into duct 8. Air may be drawn in through outlet 9 also in the rest position, i.e. before tool 40 has opened seal 16 of the associated chamber 24. After opening the webs with spike 41 dip partly into the medium. Thereby spike 41 can urge cup bottom 17 against face 62.

The free end of arbor 36 forms radially resilient tongues 45 since its shell is traversed in plane 60 by two opposed openings 46. Spring ends provided by tongues 45 are located on both sides of plane 60 and each have at the outer circumference a protruding cam 48 to which a countermember or stop 47 is coordinated. The inner circumference of projection 21 has stops 47 which are spaced from and located between the ends of projection 21. Stop 47 is a bottom projection of an axial groove 57 and located between this groove's ends. Groove 57 extends up to both ends of projection 21. Such grooves 57 with stops 47 may be mutually opposed on the inner circumference of projection 21 or on one side only. In the rest position the individual cam 48 abuts on the associated stop 47 to thus form a captive lock or catch 48, 57 against withdrawal. Thereby tongue 45 is non-tensioned and cam 48 has a minor rotative play. Thus also in the rest position an anti-rotation safeguard is provided.

When subjected to a sufficiently high withdrawal force cam 48 and tongue 45 are commonly urged radially inwards on an inclined face of stop 47. Thus bodies 4, 5 can be totally separated. Body 6 can then be removed and replaced by a filled one. As soon as arbor 36 has attained projection 21 on assembly the anti-twist safeguard 47 begins to be effective. On further insertion the cam 48 automatically hurdles cam 47. When bodies 4, 5 are rotated out of orientation in the rest position, the free ends of jacket 26 and shell 32 have a minimal gap spacing from each other permitting mutual contact. On rotation cam 48 slides over the side flank of groove 57 while tongue 45 resiliently flies radially inwards. Cam 48 then slides with increased friction on the inner circumference of projection 21 until it, respectively the other cam 48, snaps into the one or the other groove 47. An inner ring shoulder of projection 21 axially locks cam 48, even in any rotational position, but axially withdrawable when the force is increased.

To thwart tamper, means 49 are provided which although enabling the locks 47, 48, 57 to engage as well as the housing parts 25, 31 to be separated, block any section of the working stroke or mutual rotation of bodies 4, 5. Therefore the opposed ends of jacket 26 and shell 32 are commonly closely surrounded by a flexible tag or tear-off web 52. Web 52 is in one part with inner jacket 26 and has a slight gap, spacing from both shells 26, 32. This gap is bridged by rupture members including nominal breaking points 51 directly at the curved outer circumference of shell 26. Each rupture member is reduced in width and thickness toward its point 51. Eight such members 51 are circumferentially evenly distributed. On being broken members 51 part smoothly and directly from the slightly widened outer circumference of shell 26. On this circumference the inner circumference of shell 3 is then able also to slide without obstruction at the break point. In a convexly curved section, tag 52 is provided on its outside with an axial slot or grip gap which is covered by an angle projection 64. The engagement of a finger nail in the gap and under the hook 64 permits the breaking open of member 52 at this location and the peeling of it circumferentially entirely off. The forcible rotating of bodies 4, 5 also results in the bursting off of member 52.

Axial actuation can be blocked in the rest position or the like by means 50 which are overcomeable by an increased pressure force. Directly after releasing these means 50 permit a significantly easier displacement. Therefore the open rim of shell 32 slides by an inner bevel 53 on the counter rim of shell 26, thereby resiliently widening shell 32. In further action spike 41 pricks seal 16. Only thereafter and after inlet 43 has penetrated ribs 39 with their end edges 54 further slit open seal 16.

Walls 26, 37, 32, 33 are circularly curved by more than 180° on both sides of axis 11 and about axes 10 of stores 7. Therebetween these walls are throated or waisted concavely. Thus concave recesses or setting handles 58 are formed on the outsides of shells 26, 32. The arc radius of each recess 58 is greater than the radius of curvature about axis 10. Recesses 58 constantly extend between and up to both handles 29, 35. Handles 58 permit reliable holding of dispenser 1 on rotating and opening or closing bodies 4, 5. Handle 58 forms a projection 59 at the inside of shell 32. Projection 59 can be slightly nearer to plane 60 than the associated portion of shell 26. The thus formed cam 59 then effects the trigger or pressure point of control 50 since cam 59 must resiliently flex radially outwards. Cams 59 are located in a middle or axial plane 61 of axis 11. Plane 61 is perpendicular to plane 60. In plane 61 also cams 48, locks 47, 57 and handles 29, 35 are located. Deck 19 too, has the cited waisted shape.

For putting to use, dispenser 1 is opened, a blister unit 6 inserted in body 4 and then body 5 is again axially put on body 4 until members 47, 48 snap in place. Now—or prior—member 52 is torn off. In overcoming the trigger point of control 50 bodies 4, 5 are compressed. Thereby spike 41 punctures seal 16 of one of both chambers 24. Before or after that stud 34 is introduced into a nostril. By inhaling through this nostril air is drawn in via the inlet opening 56 and passages 55. This air entrains the powder from chamber 24 while flowing free of any valve from inlet 56 to outlet 9 and into the nostril. After this, stud 34 is removed from the nostril and by gripping handles 58 bodies 4, 5 are manually pulled away from each other into their rest position. Bodies 4, 5 are then mutually twisted in direction 14 through 180°. Thus the second chamber 24 is in-line with stud 34. In the same way as in the first instance the medium is then delivered from this chamber 24 into the other nostril. Thereby control 50 is likewise effective.

Figures 1, 6, 7:
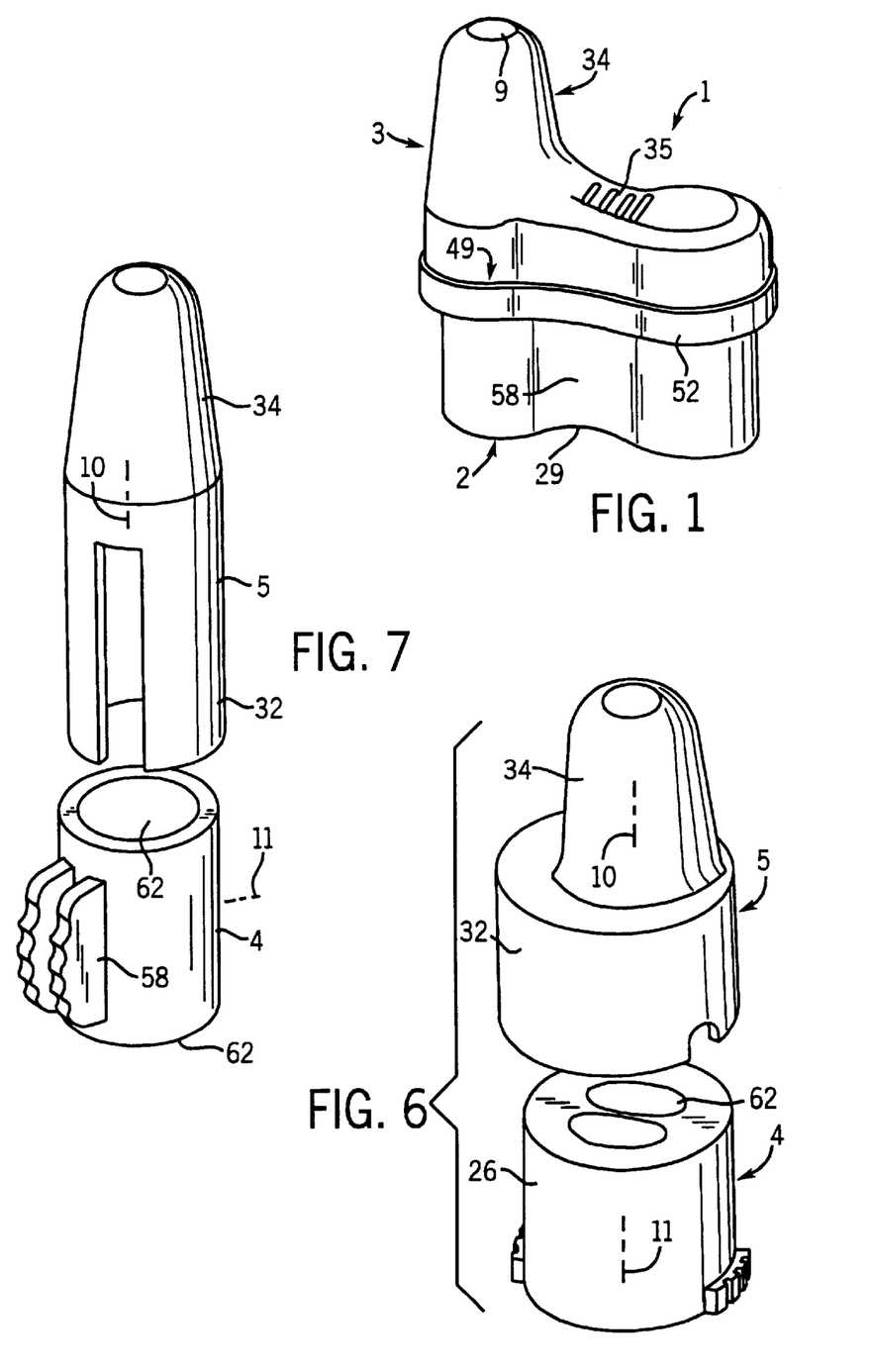
FIG. 1 is a perspective illustration of the dispenser according to the invention.
FIG. 6 is an exploded view in perspective of a further embodiment.
FIG. 7 is an exploded view in perspective of a third embodiment
Figure 2:
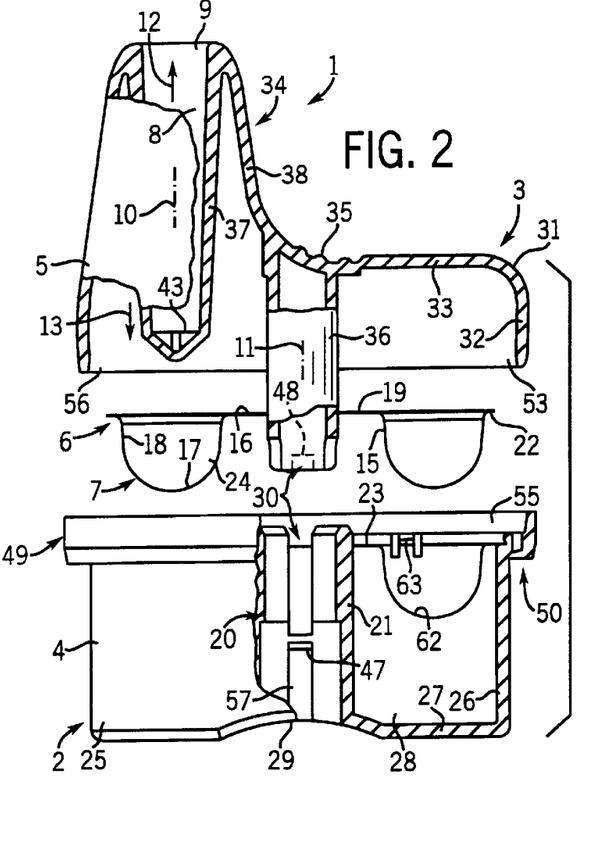
FIG. 2 is an exploded sectional view of the dispenser.
Figure 3:
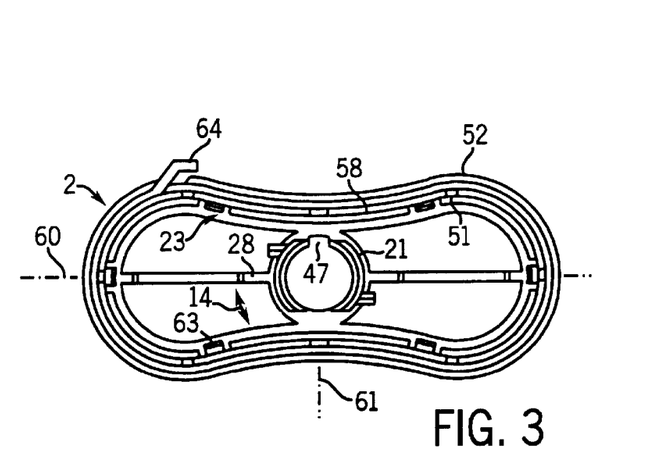
FIG. 3 is a view of the one base body as seen from above
Figure 3A:
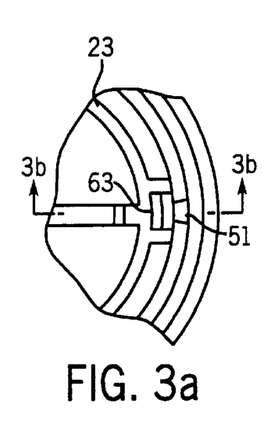
FIG. 3a is an enlarged detail view of an end portion of FIG. 3.
Figure 3B:
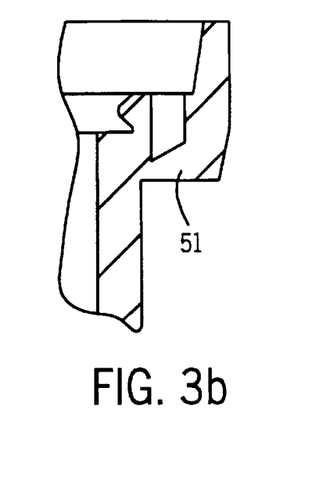
FIG. 3b is detail sectional view taken in the plane indicated by line 3b—3b in FIG. 3a, FIG. 4 is a view of the other base body as seen from below
Figure 4:
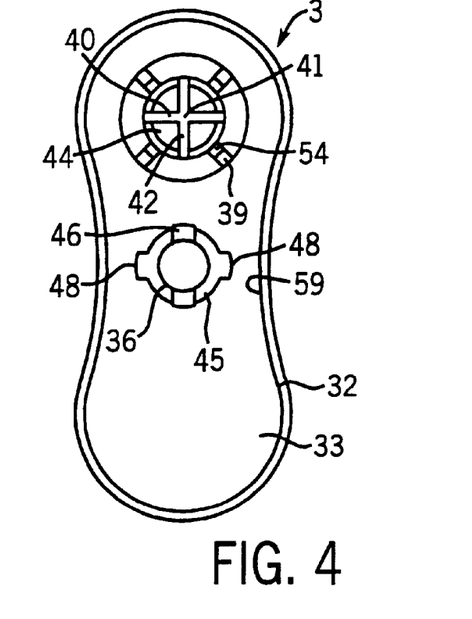
Figure 5:
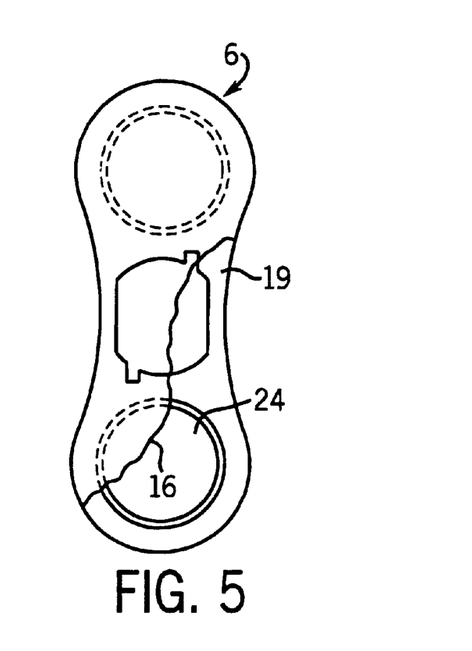
FIG. 5 is a view of the blister pack as seen from above

In FIG. 6 shells 26, 32 of bodies 4, 5 are cylindrical and each directly mutually guided solely by their circumferential faces. Stud axis 10 is eccentric to axis 11 of the shells 26, 32. Therefore blister holders 62 are directly adjacent, except for a gap spacing, without a bearing inbetween.

In FIG. 7 reversing axis 11 is transverse or perpendicular to axis 10. Axes 10, 11 may intersect. Cylindrical body 4 has on each of its two remote end faces a store place 62 for receiving an individual store. After discharge from the first individual store body 4 is totally released from body 5, reversed about its transverse axis 11 and reinserted into body 5 for discharging the second individual store. Body 5 or its shell 32 does not radially protrude beyond stud 34 while being coaxial. Shell 32 may have a length slot for the protruding engagement of handle 58 of body 4.

The proportions as illustrated are particularly favorable. It will be appreciated that all features of any one embodiment may be included in any other embodiment by being added thereto or combined therewith. The cited properties and effects may be provided precisely as described, or merely substantially or approximately so and may also greatly deviate therefrom depending on the particular requirements.

Means are included for preventing low grade discharge of the medium during breaking through or entirely opening closure 16 with tool 40. These means may prevent air flow or compressive action into chamber 24 due to constricting the casing chamber commonly bounded by units 2, 3 or bodies 4, 5 by providing a temporary bypass for such flow apart from chamber 24, opening 9, 44 or ducts 8, 55, 56. The bypass may include escape orifices like slots directly traversing at least one of the casing chamber's walls 26, 27, 29, 32, 33, 35, 37, 38. The orifices directly connect the casing chamber with the environment and commonly define a smallest passage cross-section bigger or flow resistances respective duct lengths smaller than the passage cross-section or flow resistances respective duct lengths of duct 55, 56. The means also may include a temporary addition closure for closing the opening of chamber 24, duct 8 or outlet 9. Means may be included for automatically closing escape orifices or for initially closing and subsequently opening the additional closures at the end of the opening stroke section and by the manual actuating force effecting the stroke motion. only after the opening stroke then stud 34 is to be inserted into the nostril.

What is claimed is:

1. A dispenser for discharging media comprising:
at least one base body (4, 5);
an outlet duct (8) supported by said at least one base body (4, 5) and including a duct inlet (43);
a medium outlet (9) supported by said at least one base body (4, 5);
a store body (6) including at least one store cup (15) and said store body (6) defining a bottom side, said at least one store cup (15) sealingly accommodating a discharge dose of a medium, said store cup (15) being closed by a store closure (16), and
means for providing a chamber (24), canal ducts (55) and an inlet flow passing said canal ducts (55) into said chamber (24) after said duct inlet (43) is engaged with said store cup (15) on opening said store closure (16) and while such a medium is discharged,
wherein at least one base body (4, 5) and said store body (6) define dispenser bodies, and
wherein at least one of said dispenser bodies has at least one external face including at least one finger recess (58) for receiving a user's finger tip, said finger recess being integral with said at least one dispenser body and extending transverse to actuating handles (29, 35) and directly connecting to said finger recess (58), and
wherein said actuating handles include a first actuating handle (29) and a second actuating handle (35) remote from said first actuating handle (35), said finger recess (58) extending up to said first actuating handle and said second actuating handle, said first actuating handle (29) being operationally linearly displaceable relative to said second actuating handle (35).

2. A dispenser for discharging media comprising:
at least one base body (4, 5);
an outlet duct (8) supported by said at least one base body (4, 5) and including a duct inlet (43);
a medium outlet (9) supported by said at least one base body (4, 5);
a store body (6) including at least one store cup (15) and said store body (6) defining a bottom side, said at least one store cup (15) sealingly accommodating a discharge dose of a medium, said store cup (15) being closed by a store closure (16), and
means for providing a chamber (24), suction ducts (55) and an inlet flow passing said suction ducts (55) into said chamber (24) after said duct inlet (43) is engaged with said store cup (15) on opening said store closure (16) and while such a medium is discharged,
said dispenser (1) defining a center axis (11), wherein in an axial view parallel to said center axis (11) and in a cross-section perpendicular to said center axis (11), said at least one base body (4, 5) has body ends and is oblong between said body ends, thereby defining a body length extension and a median plane (61) of said body length extension oriented transverse to said center axis (11), in the axial view and in the cross-section said at least one base body (4, 5) being acutely widened substantially from said median plane (61) toward both said body ends, said median plane (61) sub-dividing said body length extension in two equally long halves.

3. A dispenser for discharging media comprising:
at least one base body (4, 5);
an outlet duct (8) supported by said at least one base body (4, 5) and including a duct inlet (43);
a medium outlet (9) supported by said at least one base body (4, 5);
a store body (6) including at least one store cup (15) and said store body (6) defining a bottom side, said at least one store cup (15) sealingly accommodating a discharge dose of a medium, said store cup (15) being closed by a store closure (16), and
means for providing a chamber (24), suction ducts (55) and an inlet flow passing said suction ducts (55) into said chamber (24) after said duct inlet (43) is engaged with said store cup (15) on opening said store closure (16) and while such a medium is discharged, said dispenser (1) defining a center axis (11), wherein in an axial view said at least one base body (4, 5) has body ends and is oblong between said body ends, thereby defining a body length extension and a median plane (61) of said body length extension, in the axial view said at least one base body (4, 5) being acutely widened substantially from said median plane toward at least one of said body ends, and wherein at least one of said body ends is circularly arced, said median plane (61) subdividing said body length extension in two equally long halves.

4. A dispenser for discharging media comprising:

at least one base body (4, 5);

an outlet duct (8) supported by said at least one base body (4, 5) and including a duct inlet (43);

a medium outlet (9) supported by said at least one base body (4, 5);

a store body (6) including at least one store cup (15) and said store body (6) defining a bottom side, said at least one store cup (15) sealingly accommodating a discharge dose of a medium, said store cup (15) being closed by a store closure (16), and means for providing a chamber (24), suction ducts (55) and an inlet flow passing said suction ducts (55) into said chamber (24) after said duct inlet (43) is engaged with said store cup (15) on opening said store closure (16) and while such a medium is discharged, said dispenser (1) defining a center axis (11), wherein in an axial view said at least one base body (4, 5) has body ends and is oblong between said body ends, thereby defining a body length extension and a median plane (61) of said body length extension, in the axial view said at least one base body (4, 5) being acutely widened substantially from said median plane toward at least one of said body ends, and wherein said at least one base body (4, 5) defines a smallest width extension transverse to said body length extension, in the axial view said body length extension being at least 2.5 to 3 times larger than said smallest width extension, said median plane (61) subdividing said body length extension in two equally long halves.

5. A dispenser for discharging media comprising:

at least one base body (4, 5);

an outlet duct (8) supported by said at least one base body (4, 5) and including a duct inlet (43);

a medium outlet (9) supported by said at least one base body (4, 5);

a store body (6) including at least one store cup (15) and said store body (6) defining a bottom side, said at least one store cup (15) sealingly accommodating a discharge dose of a medium, said store cup (15) being closed by a store closure (16), and means for providing a chamber (24), suction ducts (55) and an inlet flow passing said suction ducts (55) into said chamber (24) after said duct inlet (43) is engaged with said store cup (15) on opening said store closure (16) and while such a medium is discharged, said dispenser (1) including at least one external depression (29, 35, 58) which is shallow, wherein said external depression (29, 35, 58) is concavely arcuated, said external depression (29, 35, 58) including a depression bottom made in one part with said at least one base body (4, 5), an external gripping face remote from said depression bottom being provided for single-handedly simultaneously gripping said depression bottom with a user's thumb and said external gripping face with the user's index finger, said store cup (15) being operationally located between said depression bottom and said external gripping face.

6. A dispenser according to claim 5 and further defining a center axis (11), wherein said at least one external depression (58) is parallel to said center axis (11).

7. A dispenser for discharging media comprising:

at least one base body (4, 5);

an outlet duct (8) supported by said at least one base body (4, 5) and including a duct inlet (43);

a medium outlet (9) supported by said at least one base body (4, 5);

a store body (6) including at least one store cup (15) and said store body (6) defining a bottom side, said at least one store cup (15) sealingly accomodating a discharge dose of a medium, said store cup (15) being closed by a store closure (16), and means for providing a chamber (24), suction ducts (55) and an inlet flow passing said suction ducts (55) into said chamber (24) after said duct inlet (43) is engaged with said store cup (15) on opening said store closure (16) and while such a medium is discharged, said dispenser (1) including at least one external depression (29, 35, 58) which is shallow and concavely arcuated, said dispenser (1) further including remote actuating handles (29, 35) and remote setting handles (58) oriented transverse to said actuating handles (29, 35), wherein said at least one external depression includes first depressions providing said actuating handles (29, 35) and second depressions (58) providing for said Setting handles for at least one of opening said dispenser, and inherently turning said dispenser (1).

8. A dispenser for discharging media comprising:

at least one base body (4, 5);

an outlet duct (8) supported by said at least one base body (4, 5) and including a duct inlet (43);

a medium outlet (9) supported by said at least one base body (4, 5);

a store body (6) including at least one store cup (15) and said store body (6) defining a bottom side, said at least one store cup (15) sealingly accomodating a discharge dose of a medium, said store cup (15) being closed by a store closure (16), and means for providing a chamber (24), suction ducts (55) and an inlet flow passing said suction ducts (55) into said chamber (24) after said duct inlet (43) is engaged with said store cup (15) on opening said store closure (16) and while such a medium is discharged, said dispenser (1) including a catch (48, 57), wherein said at least one base body (4, 5) includes subbase bodies including a first subbase body and a second subbase body axially and rotationally displaceable relative to said first subbase body, said catch (48, 57) preventing said second subbase body from being rotated relative to said first subbase body but being releasable by rotationally stressing said second subbase body relative to said first subbase body.

9. The dispenser according to claim 8, wherein said catch (48, 57) includes a stop (47) on said at least one base body (4) which forms an abutment for a second base body (5) on said first base body (4) to prevent withdrawal of said second base body (5) from said first base body (4).

10. The dispenser according to claim 8,
   further comprising a second base body (5) which is positioned on said first base body for rotation to at least one of two rotational positions, and wherein said catch (48, 57) prevents said second base body (5) from being rotated to said at least one of the two rotational positions and from being withdrawn from said first base body (4) from said at least one of the two rotational positions.

11. A dispenser for discharging media comprising:
   at least one base body (4, 5);
   an outlet duct (6) supported by said at least one base body (4, 5) and including a duct inlet (43);
   a medium outlet (9) supported by said at least one base body (4, 5);
   a store body (6) including at least one store cup (15) and said store body (6) defining a bottom side, said at least one store cup (15) sealingly accommodating a discharge dose of a medium, said store cup (15) being closed by a store closure (16), and
   means for providing a chamber (24), suction ducts (55) and an inlet flow passing said suction ducts (55) into said chamber (24) after said duct inlet (43) is engaged with said store cup (15) on opening said store closure (16) and while such a medium is discharged,
   wherein for supporting said store body (6) said at least one base body includes a support shoulder (23) which is countersunk, for positionally securing said store body (6) said base body including at least one snap member (63) opposing said support shoulder (23) and resiliently displaceable while positively preventing said store body (6) from lifting off from said support shoulder (23).

12. A dispenser for discharging media comprising:
   at least one base body (4, 5);
   an outlet duct (8) supported by said at least one base body (4, 5) and including a duct inlet (43);
   a medium outlet (9) supported by said at least one base body (4, 5);
   a store body (6) including at least one store cup (15) and said store body (6) defining a bottom side, said at least one store cup (15) sealingly accommodating a discharge dose of a medium, said store cup (15) being closed by a store closure (16), and
   means for providing a chamber (24), suction ducts (55) and an inlet flow passing said suction ducts (55) into said chamber (24) after said duct inlet (43) is engaged with said store cup (15) on opening said store closure (16) and while such a medium is discharged, wherein said store cup (15) includes a cup bottom (17) defining a cup axis (10), said at least one base body includes a bottom support (62) bridging said cup axis (10) and supporting said cup bottom (17).

13. A dispenser for discharging media comprising:
   at least one base body (4, 5);
   an outlet duct (8) supported by said at least one base body (4, 5) and including a duct inlet (43);
   a medium outlet (9) supported by said at least one base body (4, 5);
   a store body (6) including at least one store cup (15) and said store body (6) defining a bottom side, said at least one store cup (15) sealingly accommodating a discharge dose of a medium, said store cup (15) being closed by a store closure (16), and
   means for providing a chamber (24), suction ducts (55) and an inlet flow passing said suction ducts (55) into said chamber (24) after said duct inlet (43) is engaged with said store cup (15) on opening said store closure (16) and while such a medium is discharged, wherein said store cup (15) includes a cup bottom (17) defining a cup axis (10), said at least one base body includes a bottom support (62) bridging said cup axis (10) and supporting said cup bottom (17),
   wherein said bottom support (62) includes a support edge bounding a recess and directly supporting at least a portion of said cup bottom (17).

14. A dispenser for discharging media comprising:
   at least one base body (4, 5);
   an outlet duct (8) supported by said at least one base body (4, 5) and including a duct inlet (43);
   a medium outlet (9) supported by said at least one base body (4, 5);
   a store body (6) including at least one store cup (15) and said store body (6) defining a bottom side, said at least one store cup (15) sealingly accommodating a discharge dose of a medium, said store cup (15) being closed by a store closure (16), and
   means for providing a chamber (24), suction ducts (55) and an inlet flow passing said suction ducts (55) into said chamber (24) after said duct inlet (43) is engaged with said store cup (15) on opening said store closure (16) and while such a medium is discharged, wherein said store cup (15) includes a cup bottom (17) defining a cup axis (10), said at least one base body includes a bottom support (62) bridging said cup axis (10) and supporting said cup bottom (17),
   wherein said store body (6) includes exclusively two individual store cups (15) which are juxtaposed and axially parallel, said individual store cups (15) being located in a common axial plane (60), said bottom support (62) including exclusively two individual supports, a rotational bearing (30) being included and located between said two individual supports (62).

15. A dispenser for discharging media comprising:
   at least one base body (4, 5);
   an outlet duct (8) supported by said at least one base body (4, 5) and including a duct inlet (43);
   a medium outlet (9) supported by said at least one base body (4, 5);
   a store body (6) including at least one store cup (15) and said store body (6) defining a bottom side, said at least one store cup (15) sealingly accomodating a discharge dose of a medium, said store cup (15) being closed by a store closure (16), and
   means for providing a chamber (24), suction ducts (55) and an inlet flow passing said suction ducts (55) into said chamber (24) after said duct inlet (43) is engaged with said store cup (15) on opening said store closure (16) and while such a medium is discharged,
   said dispenser (1) including a support shoulder (23) for peripherally supporting said store body (6) around said store cup (15) and relative to said at least one base body (4, 5), said support shoulder (23) including a substantially annular shoulder enveloping said at least one store cup (15) and having radially inner and outer shoulder boundaries, said annular shoulder being curved, such that at least one of said radially inner and outer shoulder boundaries individually includes at least one convex boundary section and at least one concave boundary section connecting to said at least one convex boundary section.

16. A dispenser for discharging media comprising:

at least one base body (4, 5);

an outlet duct (8) supported by said at least one base body (4, 5) and including a duct inlet (43);

a medium outlet (9) supported by said at least one base body (4, 5);

a store body (6) including at least one store cup (15) and said store body (6) defining a bottom side, said at least one store cup (15) sealingly accommodating a discharge dose of a medium, said store cup (15) being closed by a store closure (16), and means for providing a chamber (24), suction ducts (55) and an inlet flow passing said suction ducts (55) into said chamber (24) after said duct inlet (43) is engaged with said store cup (15) on opening said store closure (16) and while such a medium is discharged, wherein said at least one base body (4) includes a tear-off web (52) for preventing said dispenser (1) from being actuated, said tear-off web (52) being releasable prior to actuating said dispenser (1).

17. The dispenser according to claim 16, wherein said tear-off web (52) is annular and bounds a grip gap for inserting a user's finger nail, nominal breaking points (51) being included and connecting said tear-off web (52) with said at least one base body (4) in one part, each of said nominal breaking points defining cross-sectional point extensions, namely a width extension and a thickness extension oriented transverse to said width extension, at least one of said cross-sectional point extensions decreasing toward said at least one base body (4).

18. A dispenser for discharging media comprising;

at least one base body (4, 5);

an outlet duct (8) supported by said at least one base body (4, 5) and including a duct inlet (43);

a medium outlet (9) supported by said at least one base body (4, 5);

a store body (6) including at least one store cup (15) and said store body (6) defining a bottom side, said at least one store cup (15) sealingly accommodating a discharge dose of a medium, said store cup (15) being closed by a store closure (16), and means for providing a chamber (24), suction ducts (55) and an inlet flow passing said suction ducts (55) into said chamber (24) after said duct inlet (43) is engaged with said store cup (15) on opening said store closure (16) and while such a medium is discharged, wherein said at least one base body includes a first subbase body (4) and a second subbase body (5) including said medium outlet (9), said first subbase body (4) including a store reception (62, 63) for non-rotationally rigidly holding said store body (6), said first subbase body (4) including a plug reception (20) for linearly being assembled with said second subbase body (5) and for holding said second subbase body (5) rotatably around an axis (11) and relative to said first subbase body (4), locking means being including for positively but releasably preventing said second subbase body (5) from being rotated about said axis (11), when said locking means are released said second subbase body (5) being rotatably mounted on said subbase body (4).

19. The dispenser according to claim 18, wherein said second subbase body (5) includes a bearing mandrel (36) rotably engaging said plug reception (20), said bearing mandrel (36) being radially resilient, on rotating said second subbase body (5) relative to said first subbase body (4) said store body (6) being displaced relative to said second subbase body (5).

* * * * *

UNITED STATES PATENT AND TRADEMARK OFFICE
CERTIFICATE OF CORRECTION

PATENT NO.    : 6,484,715 B1
DATED         : November 26, 2002
INVENTOR(S)   : Ritsche et al.

It is certified that error appears in the above-identified patent and that said Letters Patent is hereby corrected as shown below:

<u>Column 4,</u>
Line 60, "1800" should read -- 180º --

<u>Column 6,</u>
Line 38, "4,5" should read -- 4, 5 -- (insert a space after "4,")

<u>Column 7,</u>
Line 59, "motion. only after" should read -- motion. Only after -- (capitalize only")

<u>Column 10,</u>
Line 37, "said Setting" should be lower case -- s -- for "setting"

<u>Column 11,</u>
Line 16, "outlet duct (6)" should read -- outlet duct (8) --

Signed and Sealed this

Thirtieth Day of September, 2003

JAMES E. ROGAN
*Director of the United States Patent and Trademark Office*